United States Patent [19]

Fay

[11] 4,336,459
[45] Jun. 22, 1982

[54] METHOD AND APPARATUS FOR DETECTING FLUORESCENCE UNDER AMBIENT LIGHT CONDITIONS

[75] Inventor: Homer Fay, Snyder, N.Y.

[73] Assignee: Union Carbide Corporation, Danbury, Conn.

[21] Appl. No.: 158,642

[22] Filed: Jun. 11, 1980

[51] Int. Cl.³ .................. F21V 9/16; G01N 21/64
[52] U.S. Cl. ............................. 250/459; 250/461 R
[58] Field of Search ............ 250/458, 459, 461 R; 356/71, 51

[56] References Cited

U.S. PATENT DOCUMENTS 3,487,210 12/1969 Hubert ........................ 250/461 R
3,663,814 5/1972 Madsen ........................ 250/461 R
3,736,428 3/1973 Monroe ........................ 250/461 R Primary Examiner—Davis L. Willis
Attorney, Agent, or Firm—J. Hart Evans

[57] ABSTRACT

Fluorescent materials such as certain metal ores are detected under ambient light conditions by observing the material through a gated aperture which is opened at predetermined intervals for periods of predetermined duration while simultaneously exposing the material to periodic pulses of fluorescent stimulating light. The frequency of the light pulse is synchronized with the frequency of the opening of the gated aperture so that the aperture is open for at least a portion of the period during which fluorescence is produced by the stimulating light pulse. Electro-optic goggles are a preferred type of gated aperture.

44 Claims, 1 Drawing Figure

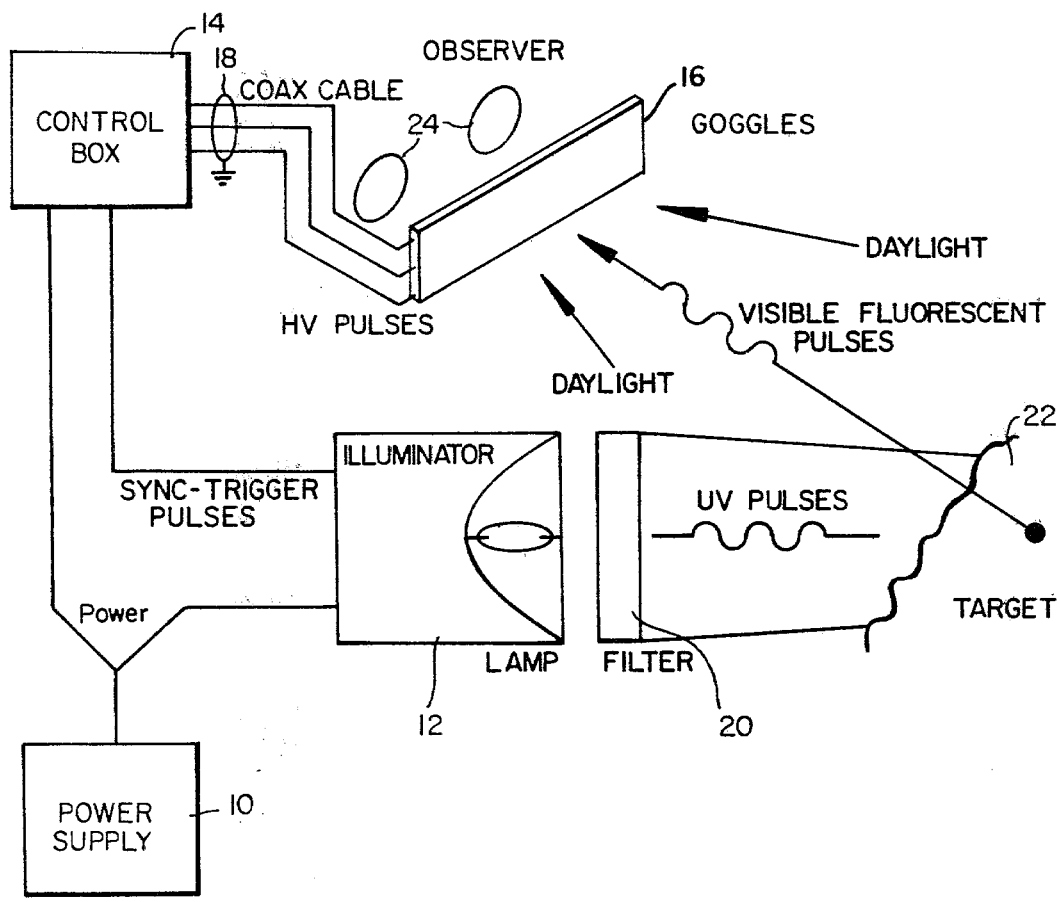

METHOD AND APPARATUS FOR DETECTING FLUORESCENCE UNDER AMBIENT LIGHT CONDITIONS

This invention relates to the detection of fluorescent material under ambient light conditions. More particularly it relates to the detection of fluorescent minerals in daylight.

The use of fluorescence in the detection and identification of minerals is well known. Many tungstates and molybdates for example, such as scheelite ($CaWO_4$), powellite ($CaMoO_4$) and their solid solutions, are strongly fluorescent. The excitation of scheelite requires short wavelength ultraviolet irradiation while powellite is excited by somewhat longer wavelengths. Prospecting for such minerals today usually involves the use of a low pressure mercury discharge lamp.

Portable mercury lamps are commercially available for mineral prospecting and are commonly used to detect scheelite in outcroppings. While such lamps are useful at night it is not possible to detect the fluorescent minerals when the background illumination is appreciable. Even bright moonlight can prevent their effective use. A further disadvantage is that the lamp must be held close to the rock to achieve sufficient radiation.

The practical disadvantages of nocturnal prospecting are several. It is of course dangerous, particularly in the more mountainous areas, because of the constant risk of slipping and falling as well as the need to guard against poisonous reptiles and insects. Another major difficulty is the problem of orientation, that is, the need to be able to recognize and identify in daylight the promising sites found at night.

It is an object of the invention therefore to provide a way to visually detect fluorescent materials under ambient daylight conditions. A further object is to provide a portable apparatus for such detection which can be conveniently carried into the field. Yet another object is to provide for such detection at a greater distance from the fluorescent material than is presently feasible.

I have now discovered that the objective of the invention can be achieved by pulsing a source of fluorescence stimulating radiation while synchronously gating the transmission of the radiation being viewed by the eye. The scene is viewed during or shortly after the pulse of stimulating radiation, during which time fluorescence is generated by the material to be detected, such as a mineral present in an ore sample. The background radiation, as from reflected sunlight, is not synchronously modulated and the perceived background radiation is effectively decreased by the attenuation or stopping of transmission to the eye for much of the time when the material is not being irradiated by the pulsed source of stimulating radiation.

Apparatus according to my invention would consist of three main elements. The first is a source of ultraviolet radiation which can be pulsed to produce short periods of intense radiation with a low repetition rate and to direct this radiation in a narrow beam toward the target. Suitable sources include lasers and flash lamps. The second element is an aperture or shutter which can be gated "on" to transmit visible optical rays with good fidelity and gated "off" to block or attenuate these rays. This can be a mechanical shutter or preferably an electro-optical modulator. The final element includes an electrical power supply and networks and logic circuits to control and synchronize the operation of the source and the aperture.

By the combination of a portable source of intense pulsed light, gated apertures in a face mask or goggles which can be worn for extended periods, portable power supply and portable control unit to synchronize the aperture and pulsed light, there is provided a device which for the first time makes it practical to prospect in daylight for fluorescent minerals. The same synergistic combination, with or without the portability feature, makes possible the visual detection of various other fluorescent materials under ambient light conditions.

In the drawing, the invention is illustrated in a block diagram.

The apparatus, which could be assembled as a blockpack unit, consists of a power supply 10, such as a twelve volt battery, which supplies power directly to an illuminator lamp 12, such as a Xenon lamp. The power supply 10 also supplies power to the control box 14. From the control box 14 synchronized trigger impulses are sent to the illuminator lamp 12 to fire it in synchronization with the electronic activation of goggles 16, which can be PLZT, through a coaxial cable 18 from the control box 14 to the goggles 16. The pulses of light are discharged from the illuminator lamp 12 by pulses from the control box 14. A filter 20 passes ultraviolet light to impinge on the target 22 while filtering out visible light. The eyes of the observer 24 thus detect the fluorescence excited in the target 24 by the pulses of ultraviolet light. Except when the observer 24 is actually seeing the fluorescence from the pulse of UV light the goggles 16 will block the daylight out, thus attenuating it to improve perception of fluorescence.

It is within the scope of the invention to substitute photographic film for the eyes of the human observer and through the use of a camera or other suitable mechanical arrangement to record the image of the fluorescent material on film.

The signal element of this invention is a source of fluorescence stimulating radiation. This can be any source which can be activated to produce pulses of radiation of sufficient strength to cause the instantaneous excited fluorescent radiation to be as strong or stronger than the bakckground radiation. Where portability is desired it is important that the power requirements of the radiation source not exceed the capabilities of a portable power source. To provide a high level of illumination, the stimulating radiation should be delivered in short pulses in an optical beam with narrow divergence.

Laser sources are particularly well suited to the requirements of this invention. Several different types of ultraviolet lasers can be used. Eximer lasers such as ArF and KrF, generate coherent ultraviolet radiation directly and the KrF laser is particularly suited to the invention. In another embodiment a gas laser such as Ar/Kr may be frequency doubled in a non-linear, harmonic generating crystal. Solid state infrared lasers such as Nd:Glass and Nd:YAG can be frequency quadrupled to produce ultraviolet rays. Such laser types are available commercially and all can be operated to produce sub-microsecond pulses of intense energy in beams with narrow beam divergence.

Flash lamps are also quite suitable for use in the invention, particularly when the distance is not great and narrow beam divergence is not critical. Xenon-filled flash lamps have been found to be particularly suited for the invention. It should be noted that Xenon-filled lamps can provide light in both the ultraviolet and the visible region of the spectrum.

The radiation source, whether laser, flash lamp or other should preferably deliver the energy in a very short pulse so that the instantaneous level of stimulation is very high and the corresponding fluorescent emission will have an intensity which instantaneously exceeds substantially the reflected background radiation. The stimulating pulse repetition frequency can be low, less than 20 Hertz, and is preferably below the flicker-fusion frequency to insure flickering fluorescence, which is preferred.

The gated aperture which attenuates the background radiation can be any device which can be gated "on", that is, actuated to open the aperture, for periods of 100 milliseconds or less with a repetition rate or frequency of 10 Hertz or more. Thus a mechanical shutter of the type used in high speed cameras could be suitable. A preferred type of shutter for the invention is the combination of two polarizer plates of opposite orientation on either side of an electrically birefringent glass, crystal or ceramic material to form a "window" which can be positioned in a viewing port or aperture, or which can be fitted into a face mask or goggles for portability. Such a window normally transmits the usual visual spectrum, but can optionally have a filter to block competing wavelengths and thus render the fluorescence more readily observed. The glass, crystal or ceramic material of the window may itself be opaque to ultraviolet light, or if it is not, a special ultraviolet filter may be used in conjunction with it in order to protect the observer's eyes.

In such a window, the pair of oppositely oriented or "crossed" polarizer sheets on opposite sides of the electrically birefringent material serves to reduce the visual transmission to a miniscule amount when the material is in the normal or "off" position, with no voltage applied. When an appropriate voltage pulse is applied to the electrically birefringent material a birefringence is induced to make the material function as a wave retardation plate. In so doing it effectively rotates the plane of polarization of the light which has passed through the first polarizer sheet so as to permit the light to pass through the second or normally "crossed" polarizer sheet.

In this "on" or open condition the window transmits up to fifty percent of the incident visual radiation. Transparent ceramics, such as lead lanthanum zirconate titanate (PLZT) are known which exhibit strong electro-optic coupling when a voltage is applied. When combined with polarizer plates that are "crossed", they provide rapid acting optical-transmission modulators which have proven particularly effective in the present invention.

The window is maintained in the "off" position, with very little visual transmission, except during a short time interval $t_1$, during which the transmission of the window is gated "on", thus opening it. This process is repeated with a period $t_2$. The pulse repetition frequency $f_2$ of the "on" state, $f_2 = 1/t_2$, is preferably chosen to be 30 Hertz or higher in order to prevent the eye of the observer from detecting flicker in the ambient illumination or normal viewing light. The relative amount of time the window is "on", referred to as the "duty cycle", is $d = t_1/t_2$. The intensity of the background radiation or ambient light perceived by the observer is equal to the unattenuated intensity times the average transmission, which is approximately the transmission in the "on" state times the duty cycle. Thus it will be seen that the perceived background intensity, or average brightness of the viewed scene, can be greatly attenuated using such an "electro-optic" window by adjusting the time intervals for a short duty cycle.

The firing or pulsing of the radiation source must obviously be coordinated and synchronized with the opening of the shutter of the aperture or viewing port. In normal operation the shutter will be opened a sufficient number of times per second to be above the so called "flicker-fusion frequency" and thus provide the observer with a relatively normal visual perception of the background radiation signal or illumination, except of course that the radiation or illumination is substantially reduced in intensity. The stimulating light source which produces the fluorescence will normally be fired less often than the shutter is opened, the firing being at a frequency which is an integral fraction of the frequency of the shutter opening.

The fluorescent pulses can thus be excited to occur with a repetition rate that is below the flicker-fusion frequency, in order to enhance the conspicuity of the fluorescent material. It is well known that flashing or pulsating lights are more readily perceived than are steady lights, in a background of steady radiation. Furthermore, the apparent brightness of such a pulsating source can be greater than that of a steady source of the same maximum intensity.

In most cases the stimulating light will be fired or energized only when the shutter is open. In those rather infrequent cases where the fluorescent decay time is relatively long the stimulating light source can advantageously be pulsed or flashed immediately before the shutter is opened.

In a typical application of the invention the window or shutter of the aperture or viewing port will be opened 48 times per second while the stimulating light will be pulsed during every eighth opening of the shutter with a repetition rate of six pulses per second. While the repetition rate of flashing the light could be as high as the frequency of the shutter opening it is normally less and is an integral fraction of the shutter frequency to insure that the pulsing of the light occurs only when the shutter or window is open. The ratio of the frequency in Hertz of the opening of the shutter or gated aperture to the pulse frequency in Hertz of the stimulating light is from about 30 to 1 to about 3 to 1. The frequency of opening the window or shutter or other gated aperture is from about 30 Hertz to about 100 Hertz. The frequency of the pulses of stimulating light is between about 3 Hertz and about 10 Hertz.

The actual means of coordinating and synchronizing the opening of the gated aperture or shutter with the pulsing of the stimulating light will of course depend upon the type of shutter and the type of stimulating light source. In general, electronic controls are preferred for their speed and reliability. Such controls are readily adjusted to varying conditions and can easily be made portable. A suitable control unit comprises an oscillator or functionally similar electronic device which, when supplied from an appropriate power source, will produce rapid primary voltage pulses at an adjustable predetermined repetition frequency. These primary voltage pulses are used to synchronize the operation of the gated aperture or shutter with the operation of the stimulating light.

In a typical embodiment of the invention the primary voltage pulses are modified by electronic circuitry to provide to the aperture secondary voltage pulses of the same repetition frequency but having a pulse width adjustable from a minimum of less than 100 microseconds to a maximum corresponding to the inverse of the repetition frequency of the primary pulses. These secondary voltage pulses, after amplification, are used to drive the gated aperture from the normal "off" or closed state to the "on" or open state, the duration of the "on" state being determined by the pulse width.

The primary voltage pulses are also directed to circuitry which serves to divide the primary pulse repetition frequency by integral amounts to produce tertiary voltage pulses to the stimulating light with a repetition frequency that is an integral submultiple of the repetition frequency of the primary pulses. The tertiary voltage pulses are modified in additional circuitry to produce sub-tertiary voltage pulses which have an adjustable pulse width variable from less than 10 microseconds to greater than 100 microseconds. The leading edges of the secondary voltage pulses and of the sub-tertiary light voltage pulses are synchronous with the leading edges of the primary voltage pulses. The trailing edges of the sub-tertiary voltage pulses to the stimulating light are detected by additional electronic circuitry, with such detection being used to trigger the discharge of power to the stimulating light source.

In this manner the occurrence of the stimulating light flash may be delayed by a time interval corresponding to the width of the sub-tertiary voltage pulse. This assures that the gated aperture or shutter will have attained the fully open state when the stimulating light pulse occurs. In another embodiment of the invention the opening of the gated aperture can be delayed by electronic circuitry in order to view a delayed fluorescent signal after the stimulating pulse has occurred.

A major utility of the present invention is in the area of prospecting for fluorescent minerals. It has been employed with particular success in the detection of scheelite, a tungsten ore. A detector unit developed for this purpose comprised a portable power pack, a portable Xenon-filled flash lamp in a case with handle, electro-optic goggles with a PLZT ceramic window and a portable electronic box with adjustable control knobs attached. The power pack employed was a 12 volt, 5 ampere hour rechargeable lead-lead dioxide battery, model CF 12V5PP sold by Eagle Picher Industries Inc. of Seneca, Mo.

The Xenon-filled flash lamp was a short-arc ultra high radiance, pulsed Xenon flash lamp in a hand-held case designated type 1190 and supplied by United States Scientific Instruments Inc. of Boston, Mass. The goggles were soft plastic welder's type goggles with, in place of the welder's glass, panels of Motorola No. 9565 PLZT material with sheets of Poloroid Corp. HN32 Polarizer on each side of the PLZT. The goggles were supplied by the Opto-Ceramic Products division of Motorola, Inc., Albuquerque, N. Mex. The control unit was assembled in a small portable box and consisted of an oscillator, several different circuit boards, a regulator board and an output board. This circuitry performed the functions described above to coordinate and synchronize the operation of the flash lamp and the goggles in the manner described above.

The power pack was connected by an electrical cable to the control unit and both were carried in a back pack. A separate cable connected the power pack to the flash lamp which was in a housing similar to that used for hand lanterns. A cable from the control unit to the flash lamp carried signals to trigger the release of the power from the power pack to produce the pulsed emissions from the lamp. A coaxial cable from the control unit to the goggle carried high voltage signals to feed power pulses to the PLZT plate and thus open the gated aperture formed by the PLZT plate and the normally crossed polarizer sheets on either side of it.

A final element in this detector unit was a control module, connected by cable to the control unit in the back pack, and small enough to be mounted near the handle of the flash lamp unit for ease of operation. This control module contained a five position switch and a control knob, both of which could be operated with the thumb of the hand holding the flash lamp unit on which the control module was mounted. The switch controlled the flow of current to the goggles as well as the pulsing of the flash lamp and could be turned fully "on" at one extreme position and fully "off" at the other. With the switch in the fully "on" position the electro-optic shutter of the goggles was fully open due to constant energization of the PLZT panel. In the three intermediate positions the goggles were pulsed at 50 Hertz and the flash lamp was pulsed respectively at 50 Hertz, 50/8 Hertz and 50/16 Hertz. In the "off" position the goggles were not energized and the flash lamp was not pulsed.

Turning the control knob of the control module varied the duration of the pulse and hence of the individual openings of the goggles, thus varying the degree to which the background radiation or illumination was attenuated. In using the detector unit with the back pack, the flash lamp housing with the control module mounted on it could be held and operated in one hand, leaving the other hand free to facilitate climbing, examination of ore samples, etc. Using this prototype detector unit, the fluorescence from samples of scheelite tungsten ore could easily be detected in full daylight at a distance of up to three to four feet.

While the invention has been described with particular reference to the detection of fluorescence in minerals such as scheelite, it is to be understood that the invention can be used to detect fluorescence from any source. Fluorescent minerals in addition to scheelite which can be detected and thus prospected for include such mineral ores as autunite, barite, calcite, calomel, cerussite, fluorite, gypsum, powellite, sphalerite, wernerite, wertzite, willemite and the like. Many precious and semiprecious gemstones such as agate, chalcedony, corundum, diamond, opal, sapphire, spinel, ruby, topaz, tourmaline and zircon may be fluorescent and can be detected. Petroleum is usually fluorescent and can be detected as can be a great number of products derived from petroleum. Fluorescent paints and dyes such as are used to find faults and flaws in commercial castings and the like can readily be detected. Another important field of potential use is in the detection of the presence of certain organic chemicals which fluoresce under suitable stimulation. These include anthracene, naphtacene, phenanthrene, pyrene, fluorene, chrysene, perylene, coronene, pentacene, acromycin, p-aminosalicylic acid, amytal, anthranilic acid, aureomycin, benzanthrene, cinchonidine, cinchonine, dibenzopyrene, folic acid, harmine, 3-hydroxyanthranilic acid, 5-hydroxyanthranilic acid, p-hydroxycinnamic acid, coumaric acid, o-hydroxybiphenyl, p-hydroxybiphenyl, kynurenine, LDS, menadione, methyl fluorene, 1-hydroxynaphthalene, 2-hydroxynaphthalene, pentobarbital, phenobarbital, plasmochin, atabrine, quinine, riboflavin, salicylic acid, terramycin, thiophenobarbital, vitamin A, xanthine and xanthurenic acid. It will be recognized that some of the above are carcinogens and others are drugs, which makes their ready detection of particular importance in many cases. Many plants and plant products fluoresce as do certain fungi. Even some animals, such as scorpions, can exhibit brilliant fluorescence. All of these can be detected with the apparatus described.

While the invention has been described with respect to visual detection, a photographic camera or other image detecting device may be substituted for the human eye, when it is desired to record the image of the fluorescent material. The gated aperture or shutter of the camera is gated open for one or more predetermined intervals, during which the pulses of stimulating radiation are synchronized to occur. By controlling the number of intervals and pulses, the exposure of the recording medium to the fluorescent radiation may be adjusted while the relative exposure of the medium to background radiation is attenuated. With properly selected film a camera or the like can also be used to record fluorescence not visible to the human eye.

What is claimed is:

1. Method of detecting visually under daylight conditions the presence of a fluorescent material, which method comprises observing said material through a gated aperture which is opened at predetermined intervals for periods of predetermined duration while simultaneously exposing said material to periodic pulses of stimulating light of a wavelength appropriate to cause fluorescence of said material, the frequency of said stimulating light pulses being synchronized with the frequency of the opening of said gated aperture, whereby said aperture is open for at least a portion of the period during which fluorescence is produced by said stimulating light pulses.

2. Method according to claim 1 wherein the wavelength of said stimulating light is in the ultraviolet region of the spectrum.

3. Method according to claim 1 wherein the wavelength of said stimulating light is in the visible region of the spectrum.

4. Method according to claim 1, 2, or 3 wherein said gated aperture is open at predetermined uniform intervals.

5. Method according to claim 1, 2, or 3 wherein said gated aperture is open for periods of predetermined uniform duration.

6. Method according to claims 1, 2, or 3 wherein said gated aperture when open is substantially transmissive of said fluorescence but is substantially opaque to said stimulating light.

7. Method according to claims 1, 2, or 3 wherein the duration of an individual opening of said gated aperture is coincident with at least a major portion of the fluorescence resulting from an individual pulse of said stimulating light.

8. Method according to claim 1, 2 or 3 wherein the duration of said individual opening of said gated aperture excludes substantially all of said pulse of said stimulating light.

9. Method according to claim 1, 2, or 3 wherein the pulse frequency of said stimulating light pulses is less than the frequency of opening said gated aperture.

10. Method according to claim 1, 2, or 3 wherein the ratio of the frequency in Hz of the opening of the gated aperture to the pulse frequency in Hz of the stimulating light pulses is from about 30 to 1 to about 3 to 1.

11. Method according to claim 1, 2, or 3 wherein the frequency of the opening of said gated aperture is above the prevailing flicker-fusion frequency.

12. Method according to claim 1, 2, or 3 wherein the pulse frequency of stimulating light is equal to or below the flicker-fusion frequency.

13. Method according to claim 1, 2, or 3 wherein the frequency of opening said gated aperture is between about 30 Hz and about 100 Hz.

14. Method according to claim 1, 2, or 3 wherein the frequency of said pulses of stimulating light is between about 3 Hz and about 10 Hz.

15. Method according to claim 1, 2 or 3 wherein the desired degree of attentuation of perceived daylight is adjusted by controlling the duration of the individual openings of said aperture up to maximum of 100 milliseconds so as to thus vary the amount of daylight admitted to the perception of the observer so as to enhance perception of the fluorescence while retaining perception of the background to the desired degree.

16. Method according to claim 15 wherein the duration of the individual opening of said aperture is less than 100 milliseconds.

17. Method according to claim 15 wherein the duration of the individual opening of said aperture is less than 100 microseconds.

18. Method of photographically detecting and recording under daylight conditions the presence of a fluorescent material, which method comprises optically projecting the radiation from said material into a photographic image recording device through a gated aperture which is opened at predetermined intervals for periods of predetermined duration while simultaneously exposing said material to periodic pulses of stimulating light of a wavelength appropriate to cause fluorescence of said material, the frequency of said stimulating light pulses being synchronized with the frequency of the said gated aperture, whereby said aperture is open for at least a portion of the time during which fluorescence is produced by said stimulating light pulses.

19. Method according to claim 18 wherein the wavelength of said stimulating light is in the ultraviolet region of the spectrum.

20. Method according to claim 18 wherein the wavelength of said stimulating light is in the visible region of the spectrum.

21. Method according to claims 18, 19 or 20 wherein said gated aperture is open at predetermined uniform intervals for periods of predetermined uniform duration.

22. Method according to claims 18, 19 or 20 wherein said gated aperture when open is substantially transmissive of said fluorescence but is substantially opaque to said stimulating light.

23. Method according to claims 18, 19 or 20 wherein the duration of an individual opening of said gated aperture is coincident with at least a major portion of the fluorescence resulting from an individual pulse of said stimulating light.

24. Method according to claim 18, 19 or 20 wherein the desired degree of attenuation of the daylight received by the recording device is adjusted by controlling the duration of the individual openings of said aperture up to maximum of 100 milliseconds so as to thus vary the amount of daylight admitted to the image recording device so as to enhance recording of the fluorescence by said image recording device.

25. Method according to claim 24 wherein the duration of the individual opening of said aperture is less than 100 milliseconds.

26. Method according to claim 24 wherein the duration of the individual opening of said aperture is less than 100 microseconds.

27. Device for the visual detection under daylight conditions of the presence of fluorescent material which comprises a pulsed source of stimulating light of a wavelength appropriate to cause fluorescence of said material, capable of pulsing at a predetermined rate, a normally closed gated viewing aperture capable of being opened at predetermined intervals for periods of predetermined duration, and control means capable of synchronizing the frequency of said stimulating light pulses with the frequency of the opening of said gated aperture.

28. Device according to claim 27 wherein the wavelength of said stimulating light is in the ultraviolet region of the spectrum.

29. Device according to claim 27 wherein the wavelength of said stimulating light is in the visible region of the spectrum.

30. Device according to claims 28 or 29 wherein said pulsed source of stimulating light is a laser.

31. Device according to claims 28 or 29 wherein said pulsed source of stimulating light is a flash lamp.

32. Device according to claims 28 or 29 wherein said pulsed source of stimulating light is a Xenon-filled flash lamp.

33. Device according to claims 27, 28 or 29 wherein said gated viewing aperture embodies a mechanical shutter.

34. Device according to claims 27, 28 or 29 wherein said gated viewing aperture embodies an electro-optic material.

35. Device according to claim 34 wherein said electro-optic material is lead lanthanum zirconate titanate.

36. Device for the photographic detection under daylight conditions of the presence of fluorescent material which comprises a pulsed source of stimulating light of a wavelength appropriate to cause fluorescence of said material, capable of pulsing at a predetermined rate, an optical system for projecting the radiation from said material into a photographic image recording device through a normally closed gated aperture capable of being opened at predetermined intervals for periods of predetermined duration, and control means capable of synchronizing the frequency of said stimulating light pulses with the frequency of the opening of said gated aperture.

37. Device according to claim 36 wherein the wavelength of said stimulating light is in the ultraviolet region of the spectrum.

38. Device according to claim 36 wherein the wavelength of said stimulating light is in the visible region of the spectrum.

39. Device according to claims 37 or 38 wherein said pulsed of stimulating light is a laser.

40. Device according to claims 37 or 38 wherein said pulsed source of stimulating light is a flash lamp.

41. Device according to claims 37 or 38 wherein said pulsed source of stimulating light is a Xenon-filled flash lamp.

42. Device according to claim 36, 37 or 38 wherein said gated viewing aperture embodies a mechanical shutter.

43. Device according to claims 36, 37 or 38 wherein said gated viewing aperture embodies an electro-optic material.

44. Device according to claim 43 wherein said electro-optic material is lead lanthanum zirconate titanate.

* * * * *